US00PP33172P2

(12) United States Plant Patent
Valin

(10) Patent No.: US PP33,172 P2
(45) Date of Patent: Jun. 15, 2021

(54) ***HELIANTHUS* PLANT NAMED 'TMSNBLEV16-1'**

(50) Latin Name: ***Helianthus* x *hybridus***
Varietal Denomination: TMSNBLEV16-1

(71) Applicant: Branded Garden Products Ltd, South Hampton (GB)

(72) Inventor: Charles Valin, Ipswich (GB)

(73) Assignee: Branded Garden Products LTD

( * ) Notice: Subject to any disclaimer, the term of this patent is extended or adjusted under 35 U.S.C. 154(b) by 0 days.

(21) Appl. No.: 17/030,105

(22) Filed: Sep. 23, 2020

(51) Int. Cl.
*A01H 6/14* (2018.01)
*A01H 5/02* (2018.01)

(52) U.S. Cl.
USPC ..... Plt./436

(58) Field of Classification Search
USPC ..... Plt./436
See application file for complete search history.

*Primary Examiner* — Annette H Para
(74) *Attorney, Agent, or Firm* — Cassandra Bright

(57) ABSTRACT

A *Helianthus* plant named 'TMSNBLEV16-1' is disclosed, characterized by a distinctive compact basalt, multi-branching habit. Plants tolerate heat well and can are suitable for vegetative propagation. The flowering period is exceptionally long, from around early Spring until mid to late Fall. Flowers are yellow with a brown center, medium-sized and fully sterile. The new plant is useful for outdoor ornamental purposes, normally produced as an outdoor garden or container plant.

3 Drawing Sheets

Genus and species: *Helianthus* x *hybridus*.
Variety denomination: 'TMSNBLEV16-1'.

BACKGROUND OF THE INVENTION

'TMSNBLEV16-1' is a product of a breeding and selection program for ornamental *Helianthus* varieties which can be vegetatively propagated. The new plant of the present invention comprises a new and distinct cultivar of *Helianthus* plant.

'TMSNBLEV16-1' is a seedling resulting from the crossing of the seed parent, an unpatented proprietary *Helianthus hybridus* referred to as 'HE15015' with the pollen parent, an unnamed, unpatented proprietary *Helianthus hybridus*. The crossing resulting in this new variety was conducted in July 2016 in Ipswich, UK. The selection of the new variety was made in July 2016, by the inventor at a research nursery located in Ipswich, UK.

'TMSNBLEV16-1' was first asexually reproduced by terminal vegetative cuttings at a greenhouse in Ipswich, UK, August 2016. The new cultivar has been found to retain its distinctive characteristics through successive asexual propagations.

SUMMARY OF THE INVENTION

The following are the most outstanding and distinguishing characteristics of the new cultivar when grown under normal horticultural practices in Suffolk, UK:

1. Compact basal multi-branching habit.
2. Medium sized (12 cm) yellow inflorescence.
3. Exceptionally long continuous blooming. Non-stop blooming May to first frosts, due to day length neutral quality.
4. Sterile flowers.
5. Heat tolerant.
6. Suitability for vegetative propagation

COMPARISON WITH PARENT VARIETIES

Plants of the new cultivar 'TMSNBLEV16-1' are similar to plants of the seed parent in most horticultural characteristics. The new variety however, differs in the following:

1. Blooming period of the new variety is May until first frost, the seed parent blooming period is July and August.
2. The new variety is totally sterile; the seed parent is pollenless but seed fertile.
3. The seed parent does not tolerate heat as well as the new variety.
4. Plants of the new variety are compact with multiple branches, plants of the seed parent are dwarf and erect.

Plants of the new cultivar 'TMSNBLEV16-1' are similar to plants of the pollen parent in most horticultural characteristics. The new variety however, differs in the following:

1. Blooming period of the new variety is May until first frost, the pollen parent blooming period is June to October.
2. The new variety is totally sterile, the pollen parent is fully fertile.
3. The pollen parent has smaller inflorescence than the new variety.

COMPARISON WITH COMMERCIAL CULTIVARS

'TMSNBLEV16-1' can be compared to the commercial variety 'Double Whammy', U.S. Plant Pat. No. 25,494. Plants of the two varieties are similar in most horticultural characteristics, however, 'TMSNBLEV16-1' differs in the following:

1. Inflorescences of the new variety are medium-sized, inflorescences of this comparator large.
2. Blooming period of the new variety is May until first frost, the blooming period of this comparator is August to October.
3. Plants of the new variety are well branched and compact, plants of this comparator are tall and upright.
4. Flowers of the new variety are single, flowers of this comparator are double.
5. Plants of the new variety tolerate heat better than plants of this comparator.

'TMSNBLEV16-1' can be compared to the commercial variety 'Table Mountain', unpatented. Plants of the two varieties are similar in most horticultural characteristics, however, 'TMSNBLEV16-1' differs in the following:

1. Inflorescences of the new variety are medium-sized, inflorescences of this comparator are small.
2. Blooming period of the new variety is May until first frost, the blooming period of this comparator is August to September.
3. Plants of the new variety are well branched and compact, plants of this comparator are upright.
4. Flowers of the new variety are fully sterile, flowers of this comparator are fully fertile.

DESCRIPTION OF THE PHOTOGRAPHS

The present invention of a new and distinct variety of *Helianthus* is shown in the accompanying photographs, the colors being as nearly true as possible with color photographs of this type.

DESCRIPTION OF THE INVENTION

Figure 1:
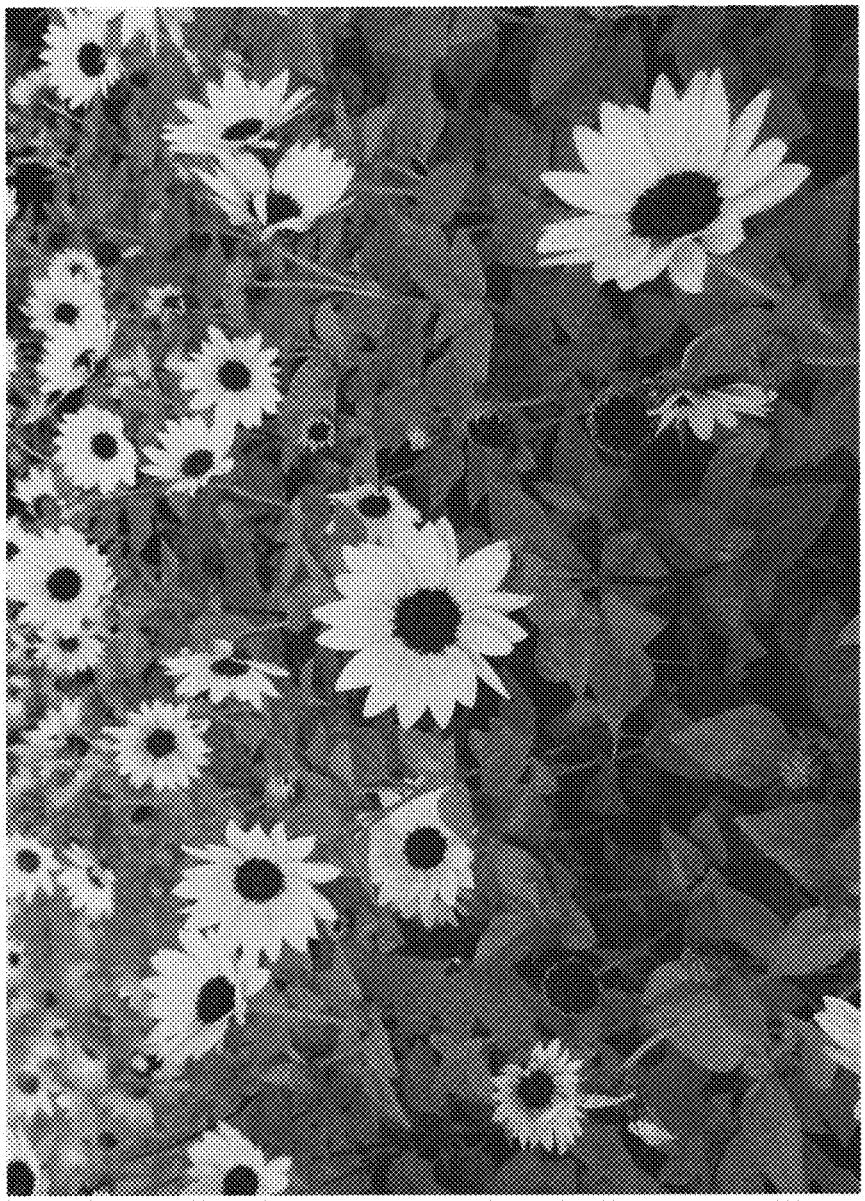
FIG. 1 illustrates several plants of the new variety at approximately 8 months of age.
Figure 2:
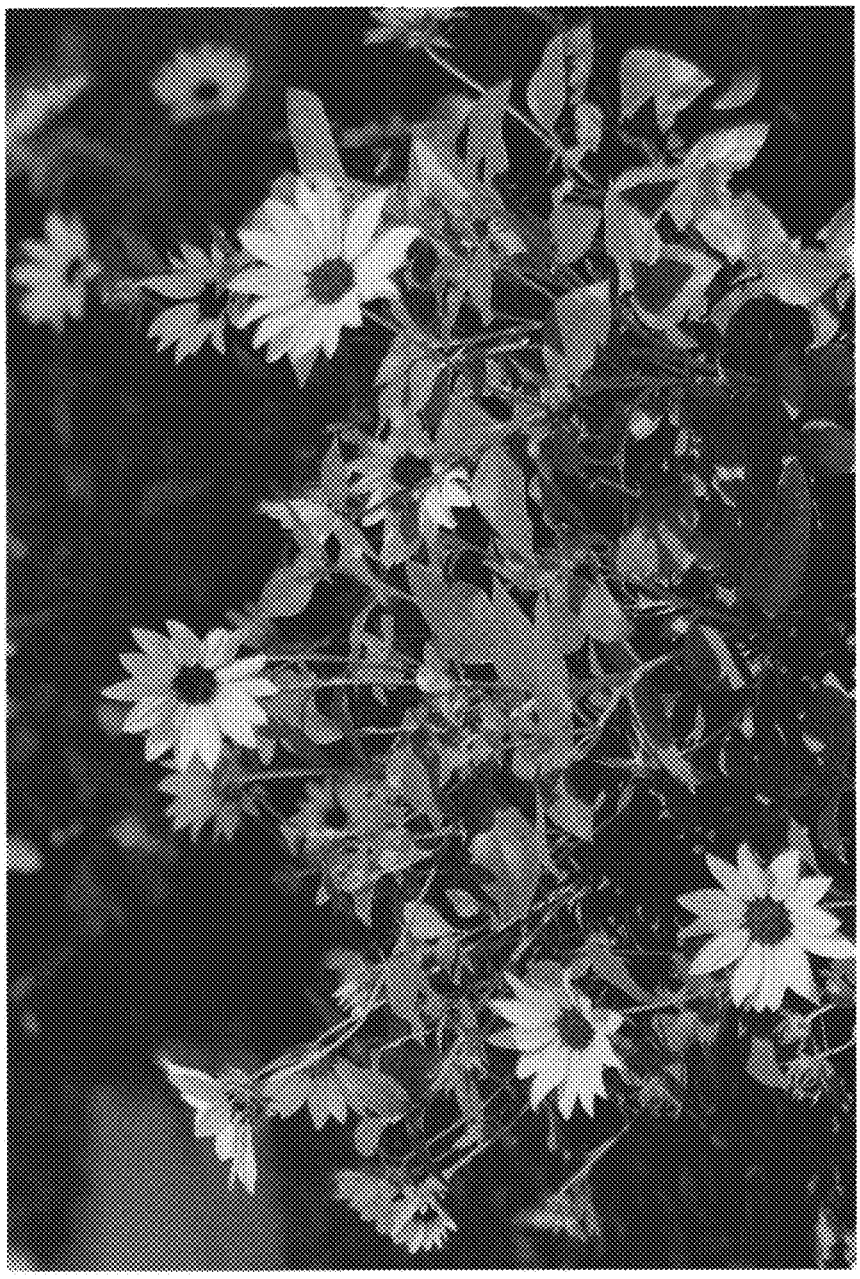
FIG. 2 illustrates a single of the new variety at approximately 8 months of age.
Figure 3:
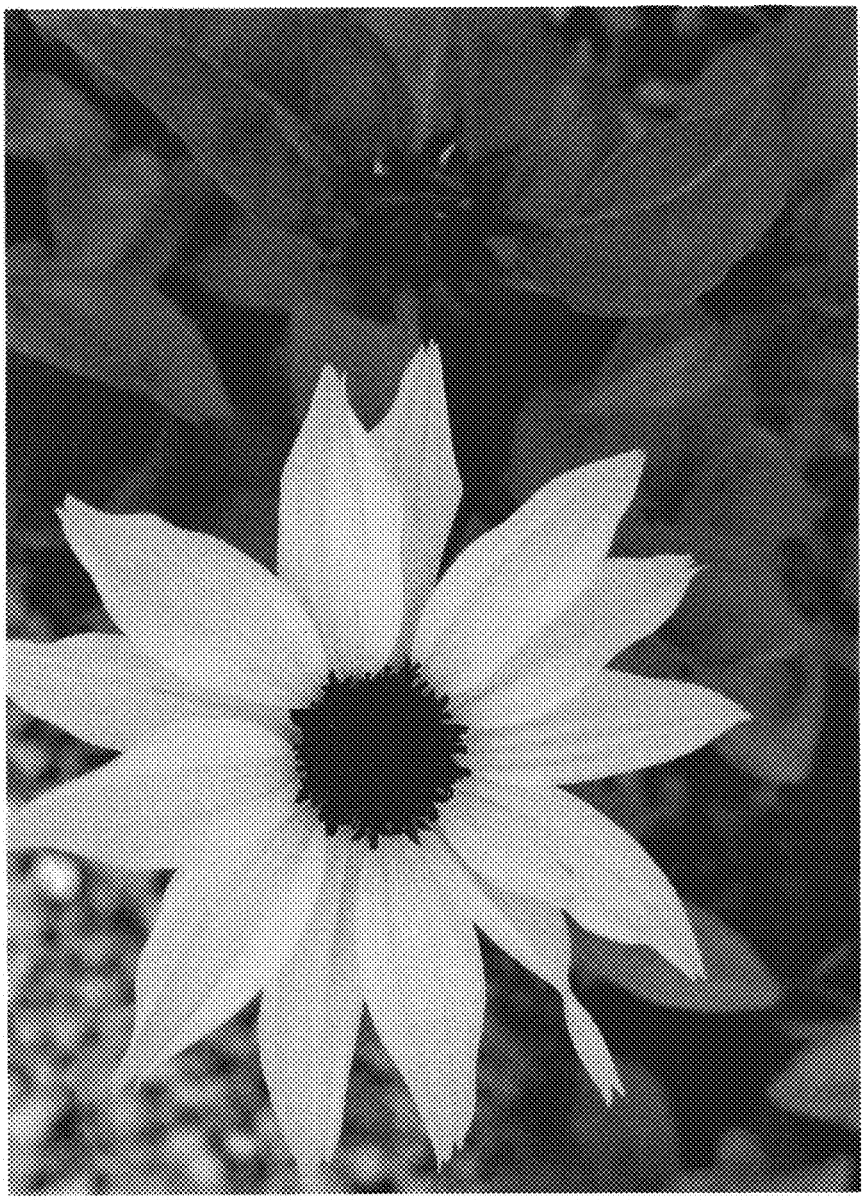
FIG. 3 illustrates a close up of the inflorescence.

This new variety of *Helianthus* is of the botanical classification *Helianthus hybridus*. The observations and measurements were gathered from plants grown outdoors in Visalia, Calif. under natural light, natural day length and temperatures. Measurements were taken during April. Plants were grown and measured in a 1-gallon pot at approximately 8 months of age.

The following is a description of the plant and characteristics that distinguish 'TMSNBLEV16-1' as a new and distinct variety. The color designations are taken from the plant itself. Accordingly, any discrepancies between the color designations and the colors depicted in the photographs are due to photographic tolerances. The color chart used in this description is The Royal Horticultural Society Colour Chart, edition 2007.

DETAILED BOTANICAL DESCRIPTION

Classification:
- *Botanical.*—*Helianthus hybridus.*
- *Denomination.*—'TMSNBLEV16-1'.

PROPAGATION

Typical method: Terminal vegetative cuttings.
Root description: Fine and fibrous brown to tan roots, not accurately measured with R.H.S. chart.

PLANT

Shape: Upright and outward.
Growth habit: Herbaceous perennial.
Growth rate: Moderately vigorous.
Height: 35 cm.
Width: 38 cm.
Branches/stems:
- *Color.*—Near RHS Yellow-Green 144B, very lightly flushed Greyed-Purple 187A.
- *Strength.*—Moderately strong and moderately flexible.
- *Length of lateral branch.*—Average range 10 to 15 cm.
- *Diameter of lateral branch.*—Average 5 to 8 mm.
- *Aspect.*—Approximately 15 to 35 degree angle.
- *Average number of lateral branches.*—6 to 8 main stems, each with 3 to 5 lateral branches.
- *Texture.*—Hirsute. Moderate density of hairs. Hairs about 1 mm long.
- *Internode length.*—Average range 3.9 to 6.8 cm.

FOLIAGE

Arrangement. Sub-opposite.
Average length: Approximately 8 to 9.5 cm, including petiole.
Average width: Approximately 3.5 to 4.5 cm.
Shape of blade: Slightly asymmetrical ovate.
Apex: Acute.
Base: Rounded and somewhat oblique.
Attachment: Stalked.
Margin: Shallow dentate.
Texture of top surface: Hirsute.
Texture of bottom surface: Hirsute.
Appearance top surface: Matte.
Appearance bottom surface: Matte.
Color:
- *Young foliage upper side.*—Near Green 137A.
- *Young foliage under side.*—Near Green 137B.
- *Mature foliage upper side.*—Near Green 137A.
- *Mature foliage under side.*—Near Green 137C.

Venation:
- *Type.*—Pinnate.
- *Venation color upper side.*—Lateral veins near Green 137B. Mid-vein near Yellow-Green 144C.
- *Venation color under side.*—Lateral veins near Green 137B. Mid-vein near Yellow-Green 144C.

Petiole:
- *Length.*—Average range 2.5 to 3.5 cm.
- *Diameter.*—2 to 3 mm.
- *Texture.*—Hirsute.
- *Color.*—Near Yellow-Green 144C, flushed Greyed-Purple N186B at attachment to stem.

FLOWER

Bloom period: May until first frost in Suffolk, UK.
Bud:
- *Bud shape.*—Broad conical.
- *Bud length.*—Approximately 2.0 cm.
- *Bud diameter.*—Approximately 1.5 cm.
- *Bud color.*—Main color near Green 137A, turning Yellow 13A towards apex.

Inflorescence:
- *Form.*—Terminal capitulum.

Inflorescence:
- *Quantity per plant.*—About 3 to 6 buds and flowers per lateral stem.
- *Diameter.*—Average 12 cm.
- *Depth.*—Approximately 4 cm.
- *Persistence.*—Ray florets self-cleaning, disc florets persistent.

Ray florets:
*Number of ray florets*.—Average range 12 to 14.
*Arrangement*.—Rotate, in a single of semi-double whorl.
*Length*.—Approximately 4.5 cm.
*Width*.—Approximately 1.2 cm.
*Apex shape*.—Acute to nearly mucronate.
*Base*.—Tapered.
*Margin*.—Entire.
*Texture*.—Smooth all surfaces.
*Aspect*.—Overall slightly reflexed down, margins upwardly curving. Linear puckered ridges.
*Appearance*.—Matte upper and lower surfaces.
Color:
Ray florets:
*Upper surface at first opening*.—Near Yellow-Orange 14A. Apex has a very thin margin near Orange-Red N34A.
*Under surface at first opening*.—Near Yellow 13A. Apex has a very thin margin near Orange-Red N34A.
*Upper surface at maturity*.—Near Yellow-Orange 14A. Apex has a very thin margin near Orange-Red N34A. Base has barely visible fine stippling near Orange-Red N34A.
*Under surface at maturity*.—Near Yellow 13A. Apex has a very thin margin near Orange-Red N34A.
Disc florets:
*Number of disc florets*.—Average range 40 to 60.
*Length*.—Approximately 4 mm.
*Width*.—Approximately 2 mm.
*Shape*.—Linear.
*Margin*.—Entire.
*Texture*.—Pubescent.
Color:
*At first opening*.—Near Brown 200A. Lower section near Yellow-Orange 15B.
*At maturity*.—Near Brown 200A. Lower section near Yellow-Orange 15B.
Fragrance: Faint, tangy scent.
Chaff:
*Quantity*.—Moderate.
*Shape*.—Linear to narrow deltate.
*Length*.—7 to 10 mm.
*Width*.—2 mm.
*Color*.—Immature: Near Yellow-White 158D. Mature: Near Brown 200B, base near White 155C.
Phyllaries/involucral bracts:
*Number*.—Average 24, in 2 or 3 whorls.
*Length*.—Average range 1.0 to 2.0 cm.
*Width*.—Approximately 4 mm to 6 mm.
*Texture*.—Upper and lower surfaces coarsely pubescent.
*Apex shape*.—Apiculate.
*Margin*.—Entire.
*Color*.—Upper surface: Apical section near Green 137B. Lower surface: Apical section near Green 137B.
Peduncle:
*Peduncle length*.—Average range 3 to 14 cm.
*Peduncle diameter*.—Approximately 3 mm.
*Aspect*.—Straight with occasional slight curvature.
*Color*.—Near Yellow-Green 145D.
*Peduncle texture*.—Hirsute. Hairs 1 to 2 mm, colored near White 155D.
Receptacle:
*Height*.—Approximately 4 mm.
*Diameter*.—Approximately 1.4 cm.
*Color*.—Near Yellow-Green 145D.
*Shape*.—Flattened.

REPRODUCTIVE ORGANS

Ray florets:
*Gynoecium*.—Not observed.
*Androecium*.—Not present.
Disc florets:
*Androecium*.—Not observed. Stamens: 2, most commonly. Style Length: About 4 mm Anther shape: Linear. Anther length: Approximately 1 mm. Anther color: Near RHS Greyed-Purple N187D. Pollen quantity: Not observed
*Gynoecium*.—Pistil number: 1. Pistil shape: Linear. Pistil length: Approx. 5 mm. Style length: Approx. 2 mm. Style color: Near White 155B. Stigma shape: 2 parted, reflexed or curled. Stigma color: Near Brown 200B.

OTHER CHARACTERISTICS

Disease and pest resistance: Neither resistance nor susceptibility to additional normal diseases and pests of *Helianthus* has been observed.
Fruit/seed production: Plants sterile, seeds not produced.

What is claimed is:
1. A new and distinct variety of *Helianthus* plant named 'TMSNBLEV16-1' as described and shown herein.

* * * * *